US011291611B2

(12) United States Patent
Elmont et al.

(10) Patent No.: US 11,291,611 B2
(45) Date of Patent: Apr. 5, 2022

(54) MULTI-LUMEN GASTROINTESTINAL FEEDING AND ASPIRATING CATHETER ASSEMBLIES

(71) Applicants: Jennifer Owens Elmont, Mapleton, UT (US); Troy J. Orr, Draper, UT (US); Stephen Dennis Minton, Provo, UT (US)

(72) Inventors: Jennifer Owens Elmont, Mapleton, UT (US); Troy J. Orr, Draper, UT (US); Stephen Dennis Minton, Provo, UT (US)

(73) Assignee: Sundance Enteral Solutions, LLC, Mapleton, UT (US)

( * ) Notice: Subject to any disclaimer, the term of this patent is extended or adjusted under 35 U.S.C. 154(b) by 320 days.

(21) Appl. No.: 16/003,974

(22) Filed: Jun. 8, 2018

(65) Prior Publication Data

US 2018/0353390 A1 Dec. 13, 2018

Related U.S. Application Data

(60) Provisional application No. 62/517,621, filed on Jun. 9, 2017.

(51) Int. Cl.
*A61J 15/00* (2006.01)
*A61M 1/00* (2006.01)
*A61M 25/00* (2006.01)

(52) U.S. Cl.
CPC ....... *A61J 15/0096* (2013.01); *A61J 15/0003* (2013.01); *A61J 15/0007* (2013.01);
(Continued)

(58) Field of Classification Search
CPC .. A61M 1/0058; A61M 1/0056; A61M 1/008; A61M 1/0037; A61M 2025/0163;
(Continued)

(56) References Cited

U.S. PATENT DOCUMENTS 3,572,315 A    3/1971  Cullen
3,658,053 A *  4/1972  Fergusson ......... A61M 25/0069
                                                         600/364
(Continued)

OTHER PUBLICATIONS

Silk , et al., "Dual-Purpose Gastric Decompression and Enteral Feeding Tubes Rationale and Design of Novel Nasogastric and Nasogastrojejunal Tubes", Journal of Parenteral and Enteral Nutrition, vol. 39, No. 5, Jul. 2015 531-543.

*Primary Examiner* — Jason E Flick
*Assistant Examiner* — Anna E Goldberg-Richmeier
(74) *Attorney, Agent, or Firm* — Stoel Rives LLP; Jordan B. Olsen (57) ABSTRACT

The embodiments disclosed herein relate to catheter assemblies. The catheter assemblies can include a multi-lumen catheter, a junction hub, and extension legs. The catheter assemblies can also include a sheath that includes a membrane that is permeable to one or more gases and impermeable to one or more liquids or solids. The catheter assemblies can be configured to deliver food to a patient through a first lumen, and simultaneously vent or aspirate one or more gases from the patient through a second lumen. The catheter assemblies can also include preformed catheters that assume a non-linear three-dimensional shape when in a relaxed state.

17 Claims, 10 Drawing Sheets

(52) U.S. Cl.
CPC ....... *A61J 15/0073* (2013.01); *A61J 15/0092* (2013.01); *A61M 1/0058* (2013.01); *A61M 1/85* (2021.05); *A61M 25/007* (2013.01); *A61M 25/0032* (2013.01); *A61J 15/0076* (2015.05); *A61M 2025/0025* (2013.01); *A61M 2025/0031* (2013.01); *A61M 2025/0037* (2013.01); *A61M 2210/0618* (2013.01); *A61M 2210/0625* (2013.01); *A61M 2210/106* (2013.01); *A61M 2210/1053* (2013.01); *A61M 2210/1064* (2013.01); *A61M 2240/00* (2013.01)

(58) Field of Classification Search
CPC .......... A61M 25/0152; A61M 25/0041; A61M 25/0045; A61M 25/0071; A61M 25/0015; A61M 25/0029; A61J 15/0015; A61J 15/0073; A61J 15/0096; A61J 15/00; A61J 15/0003
See application file for complete search history.

(56) References Cited

U.S. PATENT DOCUMENTS

| | | | |
|---|---|---|---|
| 3,893,448 A | 7/1975 | Brantigan | |
| 3,981,297 A | 9/1976 | Dunn et al. | |
| 4,016,864 A | 4/1977 | Sielaff et al. | |
| 4,221,567 A | 9/1980 | Clark et al. | |
| 4,274,417 A | 6/1981 | Delpy | |
| 4,340,615 A * | 7/1982 | Goodwin | G01N 27/40 427/2.12 |
| 4,543,089 A | 9/1985 | Moss | |
| 4,642,092 A | 2/1987 | Moss | |
| 4,901,727 A | 2/1990 | Goodwin | |
| 5,334,167 A | 8/1994 | Cacanower | |
| 5,401,241 A | 3/1995 | Delany | |
| 5,417,664 A * | 5/1995 | Felix | A61J 15/0003 604/129 |
| 5,423,320 A | 6/1995 | Salzman et al. | |
| 5,460,603 A | 10/1995 | Desantis | |
| 5,520,662 A | 5/1996 | Moss | |
| 5,807,311 A | 9/1998 | Palestrant | |
| 5,832,920 A | 11/1998 | Field | |
| 6,029,076 A | 2/2000 | Fidian-Greene et al. | |
| 6,447,472 B1 | 9/2002 | Moss | |
| 6,659,974 B1 | 12/2003 | Moss | |
| 6,949,092 B1 | 9/2005 | Moss | |
| 7,404,807 B2 | 7/2008 | Callaway | |
| 8,257,306 B2 | 9/2012 | Grathwohl | |
| 8,784,602 B2 | 7/2014 | Schaeffer et al. | |
| 9,028,441 B2 | 5/2015 | Kuhn | |
| 9,427,378 B2 | 8/2016 | Dziak et al. | |
| 2003/0144623 A1* | 7/2003 | Heath | A61M 25/0023 604/4.01 |
| 2004/0034320 A1* | 2/2004 | Burnett | A61J 15/0015 604/96.01 |
| 2004/0167463 A1 | 8/2004 | Zawacki et al. | |
| 2005/0124932 A1 | 6/2005 | Foster et al. | |
| 2005/0124935 A1 | 6/2005 | McMichael | |
| 2005/0171468 A1* | 8/2005 | Wood | A61M 3/0283 604/39 |
| 2006/0270974 A1* | 11/2006 | Goff | A61M 1/79 604/93.01 |
| 2008/0077043 A1 | 5/2008 | Malbrain et al. | |
| 2009/0048559 A1 | 2/2009 | Grathwohl | |
| 2009/0318897 A1 | 12/2009 | Bailey et al. | |
| 2011/0196290 A1 | 8/2011 | Quinn | |
| 2011/0196316 A1 | 8/2011 | Quinn | |
| 2012/0283627 A1 | 11/2012 | Moss | |
| 2013/0324916 A1 | 12/2013 | Quinn | |
| 2013/0324971 A1 | 12/2013 | Quinn | |
| 2014/0276633 A1 | 9/2014 | Visveshwara | |
| 2014/0323966 A1 | 10/2014 | Dziak et al. | |

* cited by examiner

MULTI-LUMEN GASTROINTESTINAL FEEDING AND ASPIRATING CATHETER ASSEMBLIES

RELATED APPLICATIONS

This application claims priority to U.S. Provisional Application No. 62/517,621, filed on Jun. 9, 2017 and titled "Multi-Lumen Gastrointestinal Feeding and Aspirating Catheter Assemblies," which is incorporated herein by reference in its entirety.

TECHNICAL FIELD

The present disclosure relates generally to catheter assemblies. More specifically, the present disclosure relates to multi-lumen catheter assemblies and related methods of use.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

The various embodiments disclosed herein generally relate to catheter assemblies. More specifically, the present disclosure relates to multi-lumen catheter assemblies and related methods of use. In some embodiments, the catheter assembly comprises a multi-lumen catheter, a junction hub, and extension legs. As further detailed below, in certain embodiments, the multi-lumen catheter assembly can be employed or otherwise used as a gastrointestinal feeding and aspirating device. For example, one lumen of the multi-lumen catheter assembly can be used as a feeding channel, and another lumen can be used as an aspiration channel. Other uses are also contemplated.

In one embodiment, the catheter assembly comprises a preformed multi-lumen catheter comprising a first lumen, a second lumen, and a first distal opening. The first distal opening can extend through a side wall of the catheter and can be in fluid communication with the second lumen. A sheath comprising a membrane that is permeable to one or more gases and impermeable to one or more liquids or solids can be disposed around at least a portion of the catheter such that it covers the first distal opening. The preformed catheter distal end (and/or an intermediate section) can also assume a non-linear three-dimensional configuration when the catheter is in a relaxed state (e.g., a state prior to and/or after deployment), and a substantially linear configuration in a deployment state (e.g., an introduction or insertion state).

In another embodiment, the catheter assembly can also be configured to couple to a vacuum source, wherein the vacuum source can be configured to reduce pressure in at least a portion of the second lumen, causing one or more gases to be drawn from the body of a patient through the distal opening and into the second lumen and/or out of the catheter assembly. The catheter assembly can also be configured such that the sheath does not prohibit flow of the one or more gases through the second lumen when the portion of the second lumen is under reduced pressure.

In another embodiment, a method of using a catheter assembly is disclosed. The method can comprise a step of inserting a distal end of a multi-lumen catheter through a nasal or oral passage and into a stomach or bowel of a patient. The method can further comprise steps of coupling a feed system to the multi-lumen catheter such that the feed system is in fluid communication with a first lumen, and delivering food from the feed system through the first lumen and into the patient. The method can also comprise simultaneously venting or aspirating one or more gases through a second lumen. These and other embodiments are further detailed below.

As set forth below, it will be appreciated that the various features disclosed herein are sometimes grouped together in a single embodiment, figure, or description thereof for the purpose of streamlining the disclosure. Many of these features may be used alone and/or in combination with one another. It will further be appreciated that many of the features disclosed herein may be used in conjunction with other catheter assemblies presently known or hereafter developed.

As used herein, the phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a catheter assembly is defined as the end closest to the practitioner during insertion or utilization of the catheter assembly. The distal end is the end opposite the proximal end, along the longitudinal direction of the catheter assembly.

Embodiments may be best understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

Figure 1:
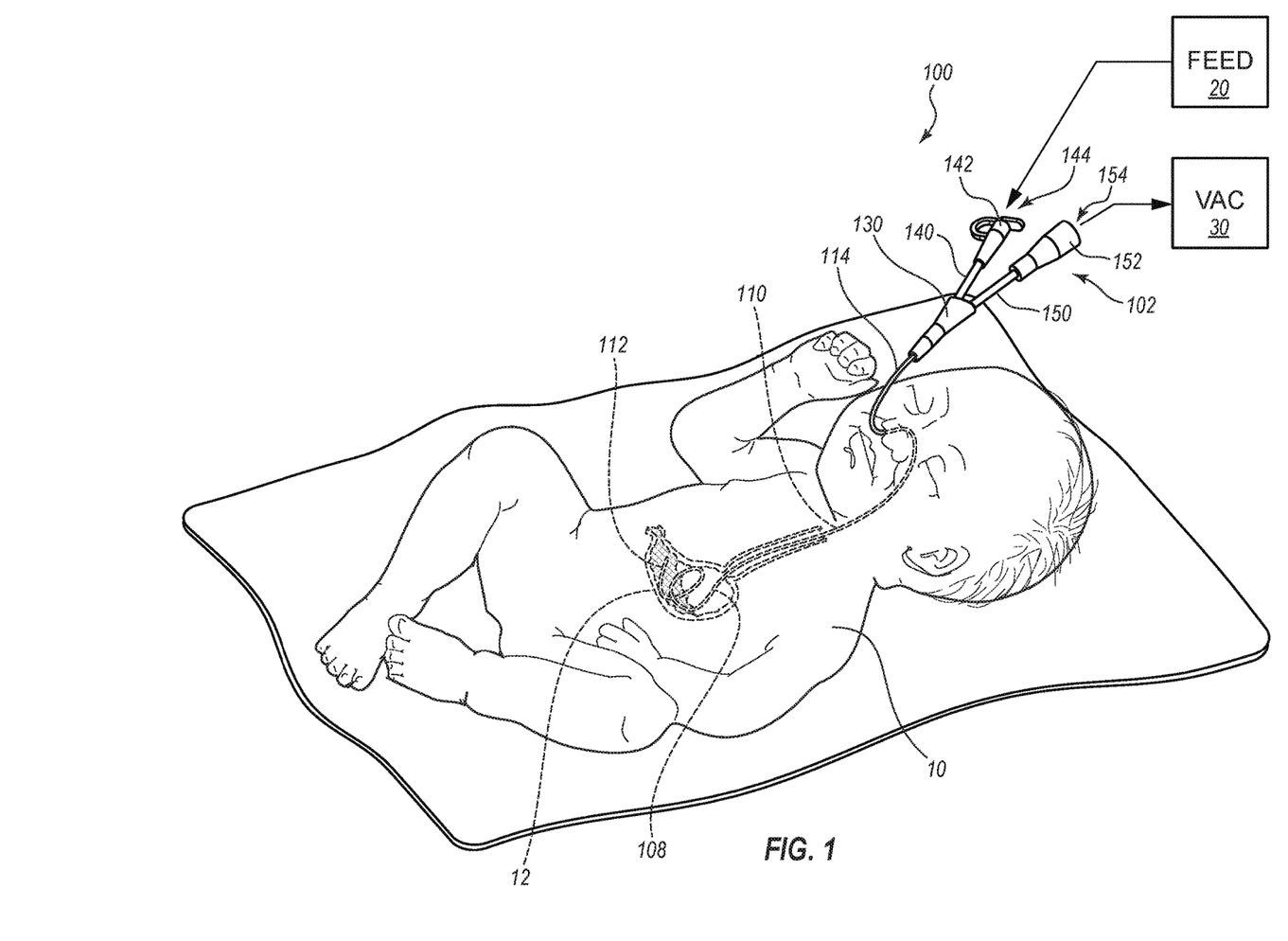
FIG. 1 is a perspective view of a multi-lumen catheter assembly being used with a patient, according to one embodiment of the present disclosure.

FIG. 1 depicts a multi-lumen catheter assembly 100 being used with a patient 10, according to one embodiment of the present disclosure. As shown in FIG. 1, the catheter assembly 100 comprises a multi-lumen catheter 110, which can also be described as a catheter 110, a catheter body 110, or an elongate member 110. The catheter assembly 100 also comprises a junction hub 130 and two or more extension legs 140, 150 (which can also be described as extension tubes 140, 150). In certain embodiments, the catheter assembly 100 further comprises one or more connectors 142, 152 (which can also be described as couplers 142, 152 or coupling members 142, 152, etc.).

When used, the catheter assembly 100 is configured to provide a passageway for components and/or substances into and/or out of a body of a patient 10. For example, in some embodiments, such as the illustrated embodiment, the catheter assembly 100 can be employed as a gastrointestinal feeding and aspirating device. For instance, the multi-lumen catheter 110 can be passed or otherwise disposed through the nasal passage (or oral passage) and into the stomach 12 (or an intestine or bowel) of the patient 10. In some of such embodiments, one lumen (e.g., a first lumen) of the multi-lumen catheter 110 can be configured to deliver a food source (e.g., a liquid food source) to a patient 10, and another lumen (e.g., a second lumen) of the catheter 110 can be configured to vent and/or aspirate one or more gases from the patient 10. As further shown in FIG. 1, in some embodiments the multi-lumen catheter assembly 100 is configured for use with an infant. However, it will be appreciated that the catheter assembly 100 can be used with patients of all ages, as desired.

Figure 8:
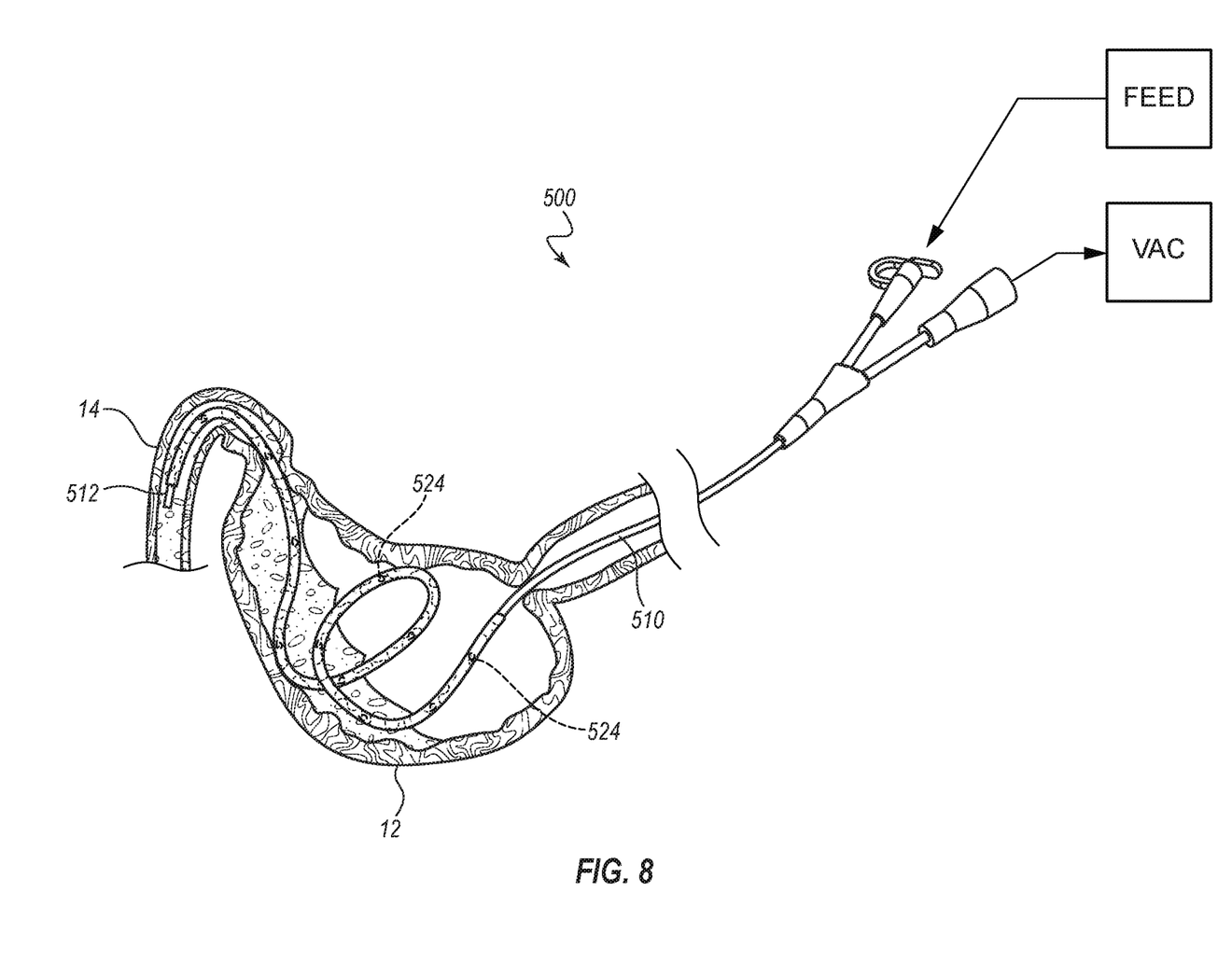
FIG. 8 is a perspective view of a multi-lumen catheter assembly, according to another embodiment of the present disclosure.

The multi-lumen catheter 110 can comprise two or more lumens, or channels, extending therethrough. For example, in some embodiments the multi-lumen catheter 110 comprises two lumens and can be referred to as a dual lumen catheter. In other embodiments, the multi-lumen catheter 110 comprises three or more lumens (e.g., one feeding lumen and two venting and/or aspiration lumens). As shown in FIG. 1, the catheter 110 also comprises a distal end 112, an intermediate section 108, and a proximal end 114. The distal end 112 is configured to be disposed in the body (or a body cavity) of the patient 10 during use. For example, in some embodiments the distal end 112 is disposed in the stomach 12 of the patient 10. In other embodiments, the distal end 112 can be disposed in an intestine (e.g., small intestine) or bowel of the patient 10 (as shown in FIG. 8.)

The proximal end 114 of the catheter 110 is configured to be disposed outside of the body of the patient 10 during use. The proximal end 114 can also be coupled to extension legs 140, 150 by a junction hub 130, as shown in FIG. 1. In other words, the proximal end 114 can be coupled to a junction hub 130, which is also coupled to extension legs 140, 150. As can be appreciated, the extension legs 140, 150 can be used to longitudinally extend one or more proximal openings or ports 144, 154 from the junction hub 130 and/or the catheter 110. Each extension leg 140, 150 comprises a lumen extending longitudinally therethrough, which provides a passageway for components and/or substances between the proximal openings 144, 154 and the junction hub 130. The junction hub 130 can then be used to couple the lumen of the first extension leg 140 to a first lumen of the catheter 110, and to couple the lumen of the second extension leg 150 to a second lumen of the catheter 110.

The proximal openings 144, 154 are disposed at the proximal end 102 of the catheter assembly 100. The proximal openings 144, 154 are configured for use in introducing and/or withdrawing various components and/or substances from the catheter assembly 100. In the illustrated embodiment, for example, a first proximal opening 144 can be used for introducing a food source (e.g., a liquid food source) to the patient 10, and a second proximal opening 154 can be used to withdraw or vent one or more gases. In certain of such embodiments, the first opening 144 can be described as a food opening or food port, and the second opening 154 can be described as a gas opening or gas port.

In some embodiments, one or more of the proximal opening 144, 154 may also extend through additional hubs, fittings, and/or connectors 142, 152, which may also be coupled to the extension legs 140, 150 and disposed at the proximal end 102 of the catheter assembly 100. As an example, one or more of the proximal openings 144, 154 may extend through a luer connector or an enteral feeding connector. Other types of hubs, fittings, and/or connectors 142, 152 can also be used as desired. Further, in some embodiments different types of connectors 142, 152 are used. For example, in some embodiments a first type of connector 142 (e.g., such as an enteral feeding connector) is coupled to the first extension leg 140, and a second type of connector 152 is coupled to the second extension leg 150. Use of different types of connectors 142, 152 can aid in identifying the different lumens of the catheter 110. For instance, a first connector 142 may be associated with a lumen of the catheter 110 that is configured to deliver a food source to the patient 10, while a second connector 152 may be associated with a lumen of the catheter 110 that is configured to withdraw or vent one or more gases.

With continued reference to FIG. 1, in some embodiments a food source or feed system 20 can be coupled to and/or otherwise used with the catheter assembly 100. For example, in some embodiments, a feed system 20 is coupled to a first extension leg 140 through a first connector 142 (e.g., such as an enteral feeding connector). Various types of feed systems 20 can be used, including but not limited to feed reservoirs, feed pumps, syringes, or other types of feed systems that are known and/or used in delivering a food source to a patient 10. As can be appreciated, food from the feed system 20 can be delivered through the first proximal opening 144, through the first extension leg 140, through the junction hub 130, through the first lumen of the catheter 110, and into the body (e.g., stomach 12) of the patient 10. In such embodiments, the first lumen of the catheter 110 can be described as being coupled to, or in fluid communication with, the first proximal opening 144 and/or the feed system 20.

Additionally, in certain embodiments, a vacuum source 30 is optionally coupled to and/or otherwise used with the catheter assembly 100. For example, in some embodiments, a vacuum source 30 is optionally coupled to a second extension leg 150 through a second connector 152. Various types of vacuum sources 30 can be used, including but not limited to vacuum pumps, syringes, or other types of vacuum sources that are known and/or used in withdrawing gases, creating a vacuum or suction, or otherwise reducing pressure. As can be appreciated, a vacuum can describe as a space having a pressure that is lower than atmospheric pressure.

The vacuum source 30 can be configured to reduce pressure in one or more regions within the catheter assembly 100, causing one or more gases to be drawn from the body (e.g., stomach 12) of the patient 10 and into a catheter lumen and/or out of the catheter assembly 100. In other words, the vacuum source 30 can be configured to aspirate one or more gases from the body (e.g., stomach 12) of the patient 10. In certain of such embodiments, the vacuum source 30 can be configured to deliver an intermittent vacuum to the catheter assembly 100. For example, the vacuum source 30 may be configured to turn on and/or off intermittently. In other embodiments, the vacuum source 30 can be configured to deliver a constant or continuous vacuum to the catheter assembly 100. In yet other embodiments, no vacuum source 30 is required, and the opening 154 can be left open for aspiration or venting at ambient conditions. For example, as gas pressure within the patient 10 builds up and exceeds the ambient air pressure, the gas can vent or aspirate out of the body of the patient 10 naturally, without the application of a vacuum from a vacuum source 30. As can be appreciated, gas from the patient 10 can be vented or aspirated by traveling from the body of the patient 10, through the second lumen of the catheter 110, through the junction hub 130, through the second extension leg 150, and out of the second opening 154. In such embodiments, the second lumen of the catheter 110 can be described as being in fluid communication with the second opening 154, and/or optionally a vacuum source 30.

In certain embodiments, the catheter assembly 100 can be configured for simultaneous feeding and aspiration. For example, at least two lumens of the catheter 110 can be separate and distinct from one another (e.g., separated by one or more inner walls). In such instances, food can be delivered through a first lumen of the catheter 110 at the same time as one or more gases are being vented or aspirated through the second lumen.

The catheter assembly 100 can also be left disposed within the patient 10 for a prolonged period of time with little or no adverse effects. For example, the catheter assembly 100 can be disposed within the patient 10 after which a first feeding session can be initiated (during which venting or aspiration can simultaneously occur with or without the use of a vacuum source 30). After the first feeding session is complete, the feed system 20 can be turned off and/or uncoupled from the first extension leg 140. Any optional vacuum source 30 being used can also be either uncoupled from the second extension leg 150, or left coupled for intermittent or continued venting or aspiration. A second feeding session can thereafter be initiated at any desired time. Additionally, an alternative feeding session can also be initiated while the catheter assembly 100 is left in place. For example, the patient 10 can be fed orally (e.g., through the mouth) while the catheter assembly 100 is disposed through the nasal passage. For instance, an infant can be bottle or breast fed orally without removal of the catheter assembly 100.

Figure 2:
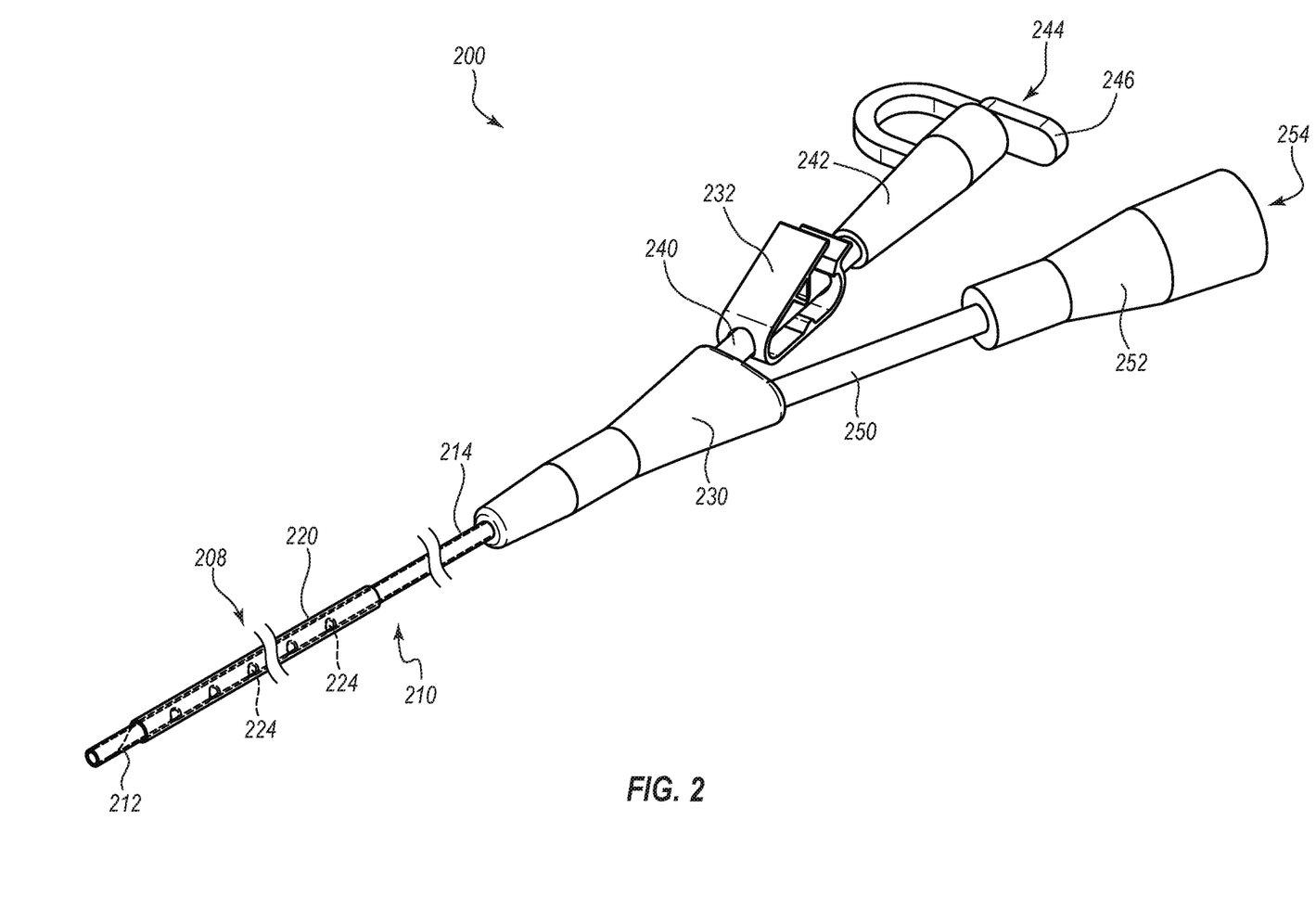
FIG. 2 is a perspective view of a multi-lumen catheter assembly, according to another embodiment of the present disclosure.

FIG. 2 illustrates a catheter assembly 200 in accordance with another embodiment of the present disclosure. The catheter assembly 200 can, in certain respects, resemble the catheter assembly 100 described above in FIG. 1. Accordingly, like features are designated with like reference numerals, with the leading digits incremented to "2." Relevant disclosure set forth above regarding similarly identified features thus may not be repeated hereafter. Moreover, specific features of the catheter assembly 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the catheter assembly 200. Any suitable combination of the features and variations of the same described with respect to the catheter assembly 100 can be employed with the catheter assembly 200, and vice versa. This pattern of disclosure applies equally to further embodiments depicted in subsequent figures and described hereafter, wherein the leading digits may be further incremented.

As shown in FIG. 2, the catheter assembly 200 comprises a catheter 210 having a distal end 212, an intermediate section 208, and a proximal end 214. The catheter assembly 200 also comprises a junction hub 230, first and second extension legs 240, 250, and first and second connectors 242, 252. As further shown in FIG. 2, in some embodiments the catheter assembly 200 also comprises a sheath 220 disposed on and/or around at least a portion of the catheter 210. For example, the sheath 220 can be disposed around at least a portion of the intermediate section 208 of the catheter 210.

In some embodiments, the sheath 220 can be configured to selectively allow passage of one or more substances into and/or out of the catheter 210. For example, in certain embodiments the sheath 220 comprises a permeable or semi-permeable membrane. In various embodiments, the membrane can allow passage of one or more gases, while restricting (or otherwise minimizing) the passage of other molecules such as liquids and solids (e.g., liquid and/or solid foods, aqueous liquids, or other bodily fluids, etc.). In other words, the membrane can be described as being permeable to one or more gases, and impermeable (or substantially impermeable) to other substances (e.g., such as liquids and solids).

Various types of membranes can be used. In some embodiments, for example, a polymeric membrane comprising a fluoropolymer is used. In more particular embodiments, a polymeric membrane comprising polytetrafluoroethylene (PTFE) is used. The polytetrafluoroethylene can also be expanded (e.g., ePTFE). Other types of polymeric membranes can also be used.

The sheath 220 or membrane can also have various degrees of selectivity. In some embodiments, the degree of selectivity (or the selectivity) of the membrane can be dependent upon the membrane pore size. For example, membranes having a larger pore size can be configured to allow passage of larger molecules, while membranes having a smaller pore size can be configured to allow passage of smaller molecules. In certain embodiments, the membrane comprises pore sizes of less than about 100 microns, less than about 50 microns, less than about 25 microns, less than about 10 microns, or less than about 5 microns. In further embodiments, the membrane comprises pore sizes of between about 0.001 microns and about 100 microns, or between about 0.01 microns and about 50 microns. In still further embodiments, the membrane comprises pore sizes of between about 0.01 microns and about 10 microns, between about 0.05 microns and about 5 microns, between about 0.1 microns and about 3 microns, or between about 0.2 microns and about 1 micron. Membranes having other pore sizes (e.g., larger or smaller) can also be used.

In certain embodiments, the sheath 220 is configured to cover one or more distal openings 224 in the catheter 210. For example, as shown in FIG. 2, the catheter 210 can comprise one or more distal openings 224 disposed on a side wall of the catheter 210. In some embodiments, the one or more distal openings 224 are disposed along a longitudinal length of the catheter 210. And in certain of such embodiments, the one or more distal openings 224 are aligned along a longitudinal length of the catheter 210. As further detailed below, the one or more distal openings 224 can extend through the side wall and can be in fluid communication with a lumen of the catheter 210 (such as a second lumen that is configured to vent or aspirate one or more gases). In such embodiments, the sheath 220 can be configured to selectively allow passage of one or more substances (e.g., gases) through the one or more distal openings 224 and into the lumen of the catheter 210, while restricting the passage of other substances (e.g., liquids or solids).

With continued reference to FIG. 2, in some embodiments, the catheter assembly 200 further comprises a clamp 232 and/or valve. For example, in some embodiments, a pinch clamp 232 is used on one or more of the extension legs 240, 250 of the catheter assembly 200. In the illustrated embodiment, for example, a pinch clamp 232 is disposed on the first extension leg 240, which can be associated with the feeding lumen of the catheter 210. In such embodiments, the pinch clamp 232 can be configured such that excess food and/or other substances do not flow backwards through the catheter assembly 200. Additionally, the connectors 242, 252 can also include caps 246 that can be configured to close the openings 244, 254 of the catheter assembly 200 as desired.

As further detailed below, in particular embodiments, one or more valves can also be used. For example, a valve can be coupled to distal end 212 (or a proximal end 214) of the catheter 210. In some embodiments, the valve can comprise a one-way valve, such that food or other substances can only flow through the valve in one direction. Use of such valves can aid in preventing backflow of food or other substances through the catheter assembly 200.

Figure 3:
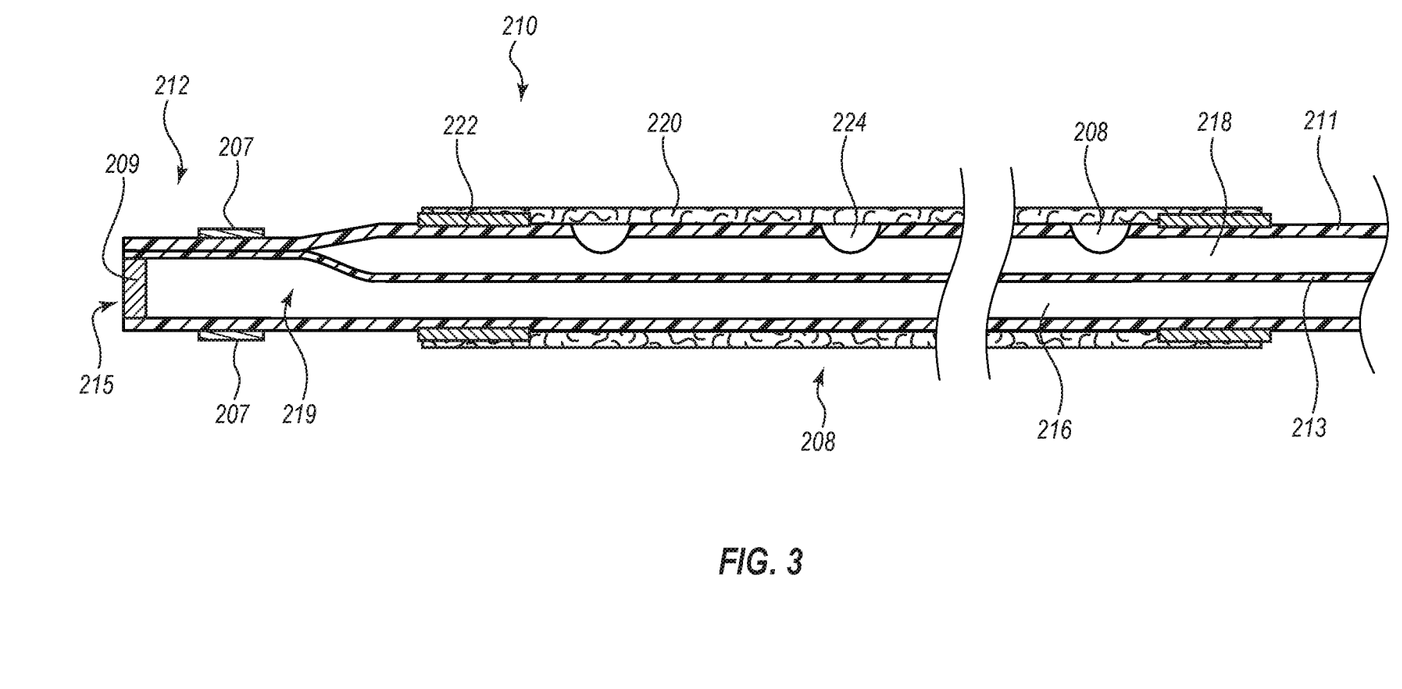
FIG. 3 is an enlarged cross-sectional view of a portion of a multi-lumen catheter assembly, such as the multi-lumen catheter assembly of FIG. 2.

FIG. 3 is a cross-sectional view of a portion of a catheter assembly, such as the catheter assembly 200 of FIG. 2. More specifically, FIG. 3 depicts a cross-sectional view of a longitudinal portion of a catheter 210. As shown in FIG. 3, the catheter 210 comprises a first and second lumen 216, 218 extending longitudinally through the catheter 210. As previously described, in some embodiments, one lumen 216 (e.g., a first lumen) can be configured for the passage of a food source, and another lumen 218 (e.g., a second lumen) can be configured for the passage of one or more gases. As shown in FIG. 3, the lumens 216, 218 are separate from one another by a wall 213 or another barrier. Further, while in the illustrated embodiment the lumens 216, 218 are disposed within a single catheter 210, it will be appreciated that in other embodiments multiple catheters can be employed and optionally coupled together. Accordingly, it will be appreciated that various types of catheter systems can be used.

As further shown in FIG. 3, the first lumen 216 can be in fluid communication with a distal opening 215 at a distal end 219 of the lumen 216. The opening 215 can be configured to allow the passage of food (that can originate from a feed system) out of the lumen 216 and into the body of a patient. In certain embodiments, a valve 209, such as a one-way valve, can be used. For example, a one-way valve 209 can be coupled in or to a distal end 219 of the lumen 216, allowing passage of a substance such as food out of the catheter lumen 216 while restricting passage of a substance from within a body cavity into the catheter lumen 216. In other embodiments, a valve 209 is not used, and the lumen 216 can comprise an opening in the distal end 212, or in a side wall adjacent thereto.

The second lumen 218 can also be in fluid communication with one or more distal openings 224. As shown in the illustrated embodiment, for example, one or more distal openings 224 can be disposed along the intermediate section 208 of the catheter 210. The one or more distal openings 224 can also be disposed on or otherwise extend through a side wall 211 of the catheter 210. In certain embodiments, the one or more distal openings 224 can be configured to allow passage of one or more gases from a body cavity into the catheter lumen 218 (e.g., for venting and/or aspiration).

As previously discussed, a sheath 220 can be disposed around the catheter 210 such that it covers the one or more distal openings 224 leading to the second lumen 218. In some of such embodiments, the sheath 220 comprises a membrane that is permeable to (or selectively allows) passage of certain molecules (e.g., such as gas molecules), and impermeable to the passage of other molecules (such as liquids and solids, etc.).

In some embodiments, the sheath 220 is coupled and/or otherwise adhered to the catheter wall 211, which can be done in various ways. For example, in certain embodiments, the sheath 220 is coupled using an adhesive, such as an epoxy, etc. The sheath 220 can also be heat sealed, wherein the sheath 220 and/or the catheter wall 211 can bond following the application of heat. The sheath 220 can also be coupled mechanically, such as using a suture, a clamp, a groove, or another type of mechanical coupling member or device.

In certain embodiments, a marker 207 such as a radiopaque marker is also disposed on the catheter 210. For example, a marker 207 can be disposed at a distal end 212 (or along the intermediate section 208) of the catheter 210. The marker 207 can be useful during placement of the catheter 210 in a body of a patient. For example, a radiopaque marker 207 can be viewed during the insertion procedure, or anytime thereafter, to ensure proper placement of the catheter 210 in the body of a patient.

Figure 4A:
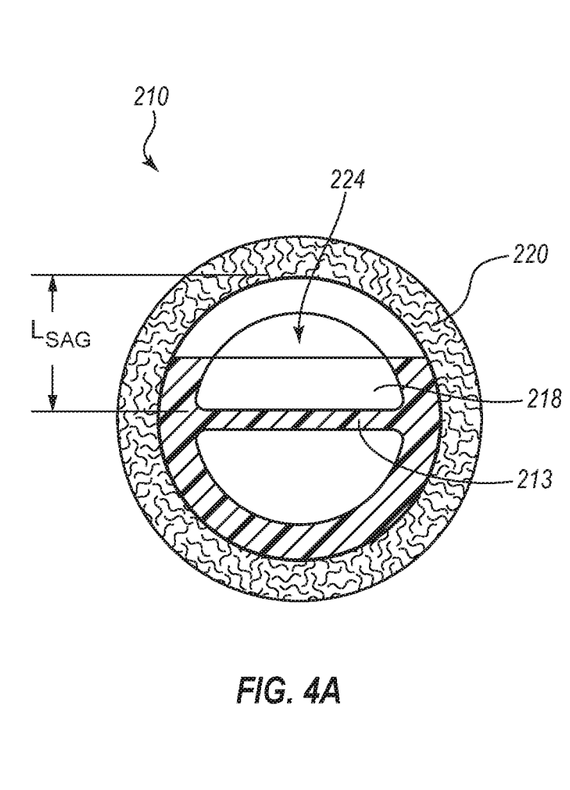
FIGS. 4A and 4B are additional enlarged cross-sectional views of a portion of a multi-lumen catheter assembly, such as the multi-lumen catheter assembly of FIG. 2.
Figure 4B:
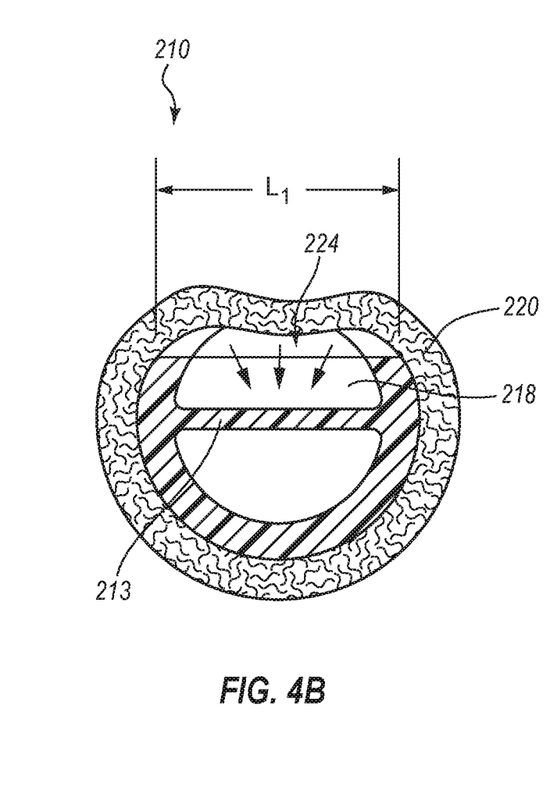
Figure 5A:
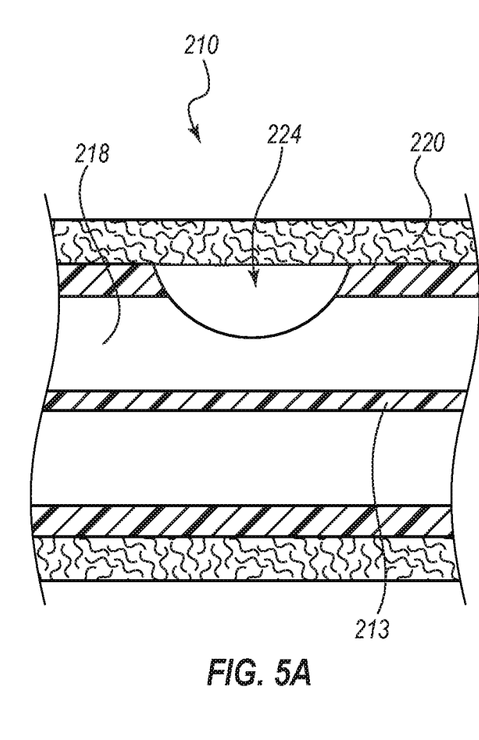
FIGS. 5A and 5B are additional enlarged cross-sectional views of a portion of a multi-lumen catheter assembly, such as the multi-lumen catheter assembly of FIG. 2.
Figure 5B:
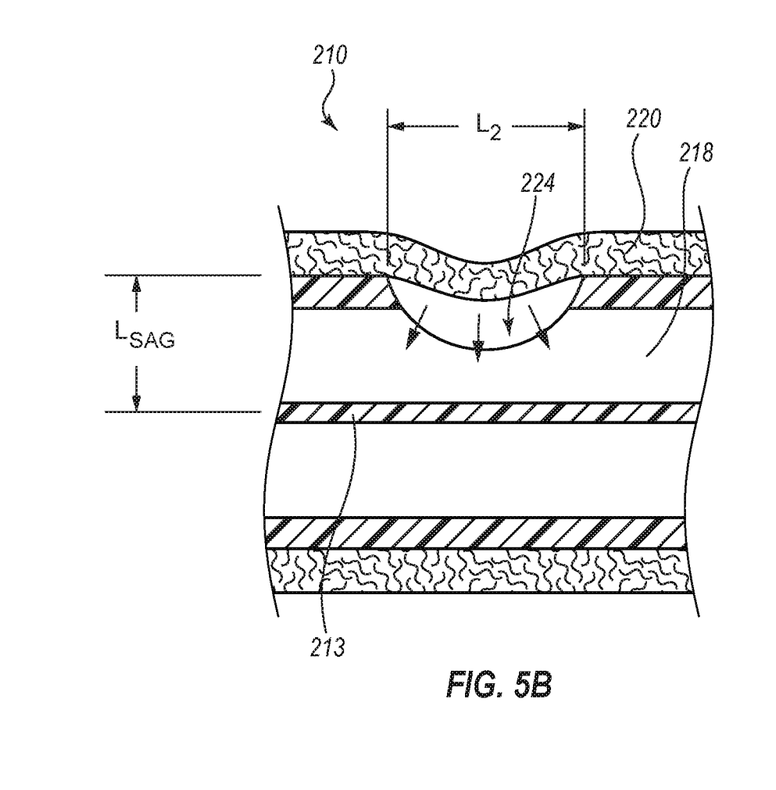

FIGS. 4A, 4B, 5A, and 5B depict additional cross-sectional views of a portion of a catheter assembly, such as the catheter assembly of FIG. 2. In particular, FIGS. 4A and 4B depict cross-sectional views of a catheter 210 that are transverse to the longitudinal length or longitudinal axis of the catheter 210, and FIGS. 5A and 5B depict cross-sectional views along a longitudinal length or longitudinal axis of the catheter 210. Further, FIGS. 4A and 5A depict a catheter 210 in a resting state, or a state in which a vacuum or reduced pressure is not being applied to the second lumen 218 of the catheter 210. FIGS. 4B and 5B depict the catheter 210 in an aspiration state, or a state in which a vacuum or reduced pressure is being applied to the second lumen 218 of the catheter 210 (as indicated by the reference arrows).

As can be appreciated, a vacuum or reduced pressure can cause a portion of the sheath 220 to be drawn or to otherwise sag inwards towards and/or through the distal opening 224. In certain of such embodiments, the catheter 210 and/or sheath 220 are configured such that the sheath 220 is restricted from clogging or otherwise blocking the lumen 218. For example, in particular embodiments, the catheter 210 and sheath 220 are configured such that the sheath 220 is restricted from being drawn into contact with the inner or back wall 213 of the lumen 218. As shown in the illustrated embodiment, for example, the distal openings 224 can be sized such that the sheath 220 is supported by the walls of the distal openings 224, preventing the sheath 220 from coming in contact with the inner wall 213.

In certain of such embodiments, one or more lengths $L_1$ and/or $L_2$ (or a diameter if circular) of the distal openings 224 can also be selected such that the walls of the distal openings 224 can support the sheath 220 and prevent the sheath 220 from being drawn inside the lumen 218 and into contact with the inner wall 213. For example, as shown in the illustrated embodiment, the sheath 220 can be prevented from being drawn in a distance of $L_{SAG}$. In some embodiments, the openings 224 are circular, such that $L_1$ is substantially equal to $L_2$. In other embodiments, the lengths of $L_1$ and $L_2$ are different. For example, the openings 224 can be non-circular, such as in the shape of an oval, a square, a slot, or a slit, etc.

Other methods can also be employed to prevent the sheath 220 from being drawn into contact with the inner wall 213 of the lumen 218. For example, in some embodiments, the material of the sheath 220 is selected such that the sheath 220 comprises a stiffness that prevents the sheath 220 from being drawn into contact with the inner wall 213. In yet other embodiments, the sheath 220 comprises a thickness that prevents the sheath 220 from being drawn into contact with the inner wall 213 of the lumen 218.

Figure 6:
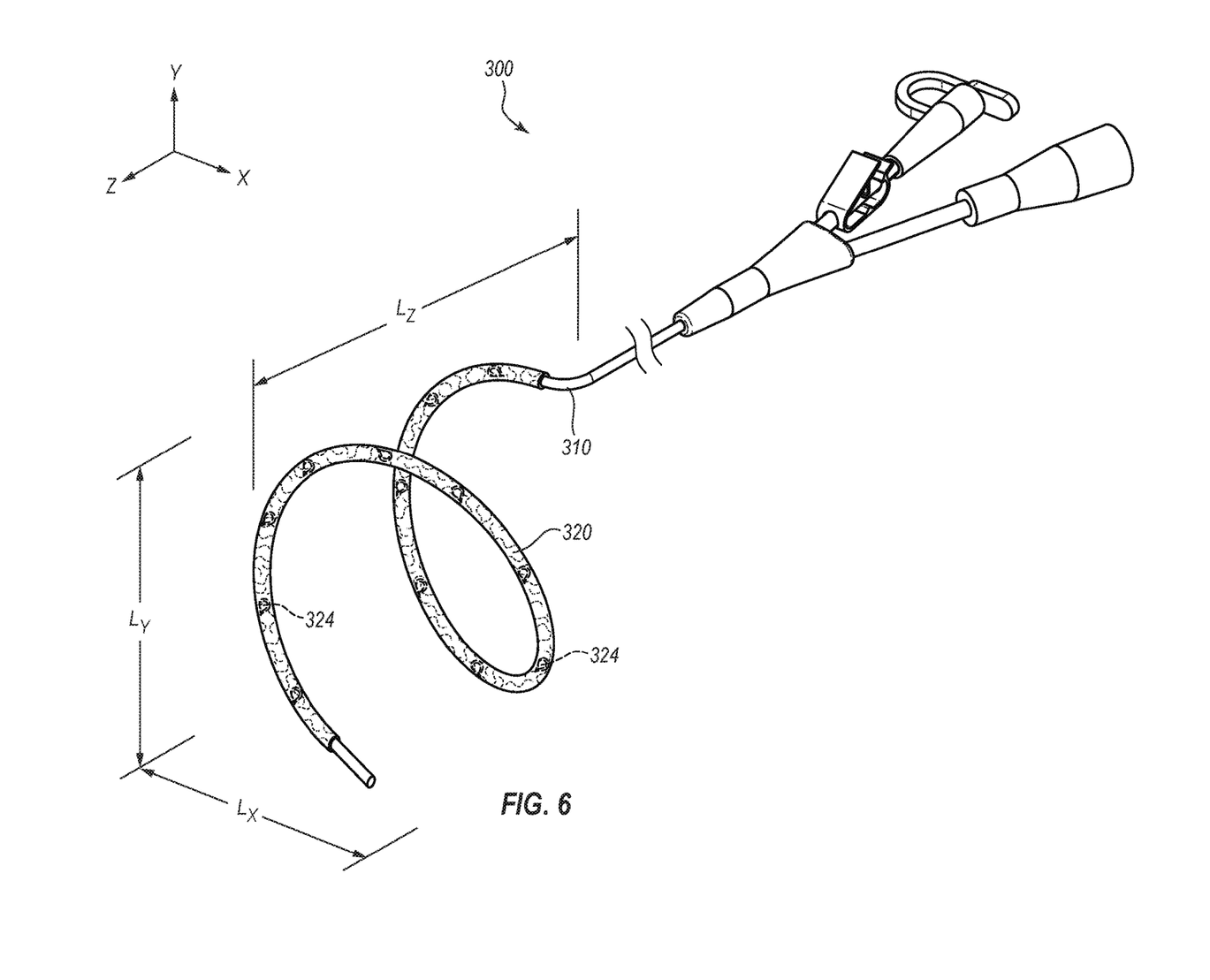
FIG. 6 is a perspective view of a multi-lumen catheter assembly, according to another embodiment of the present disclosure.

FIG. 6 depicts a catheter assembly 300 in accordance with another embodiment of the present disclosure. As shown in FIG. 6, in some embodiments, the catheter 310 comprises a preformed catheter 310. A preformed catheter 310 can be described as a catheter 310 that assumes a predetermined, non-linear shape in its relaxed state. In other words, the catheter 310 assumes a specified shape that is non-linear when not being acted upon by one or more outside forces. Further, a preformed catheter 310 can re-assume or at least partially recover to its predetermined, non-linear shape after temporary application of an outside force. In some embodiments, the relaxed state can be used in reference to a state of the catheter 310 prior to and/or after deployment in a body cavity. In other embodiments, the catheter is not preformed. For example, the catheter can be substantially linear, such as can be represented by the catheter assembly depicted in FIG. 2.

Figure 7:
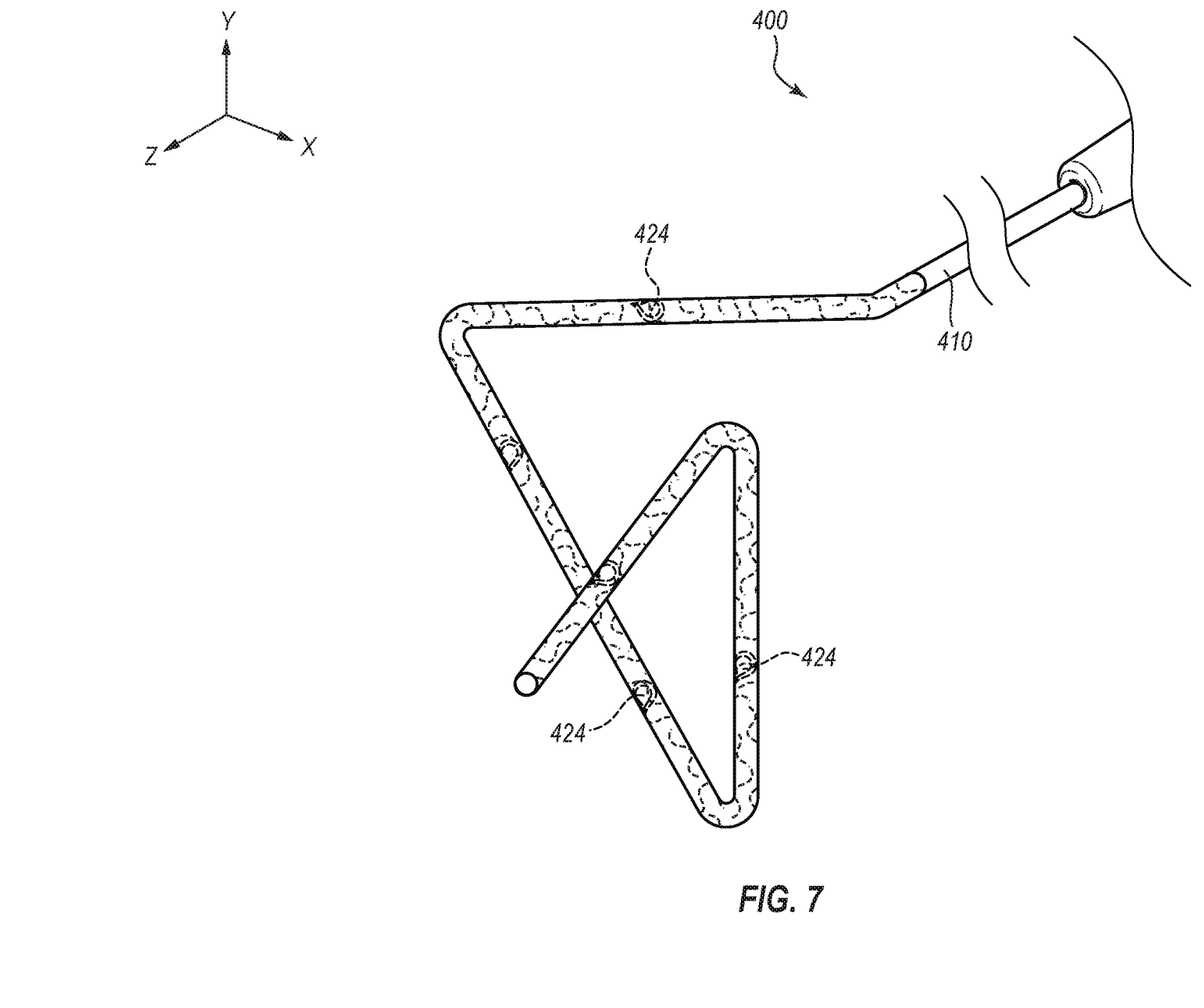
FIG. 7 is a perspective view of a portion of a multi-lumen catheter assembly, according to another embodiment of the present disclosure.

The preformed catheter 310 can assume any variety of shapes in its relaxed state, including three-dimensional shapes in which portions of the catheter 310 extend along two or more of the X, Y, and Z axes. For example, in the illustrated embodiment the catheter 310 extends along a distance $L_Z$ in the Z axis, a distance $L_Y$ in the Y axis, and a distance $L_X$ in the X axis. In particular embodiments, the preformed catheter 310 can assume a helical, a spiral, or a coil-like shape in its relaxed state (such as is shown in FIG. 6). In other embodiments, the preformed catheter 310 can assume a non-defined three-dimensional shape in its relaxed state (such as is shown in FIG. 7).

In some embodiments, the preformed catheter 310 comprises a resilient material such that it can be temporarily straightened or substantially straightened for insertion into the body of a patient. For instance, the preformed catheter 310 can be in a first state prior to deployment, wherein the catheter 310 comprises a predetermined shape in the first state. The preformed catheter 310 can then be configured to transition to a second state during deployment (e.g., an introduction or insertion state). For instance, the preformed catheter 31 can be straightened or substantially straightened along a guide wire, stylet, or with another insertion aid. For example, an outer insertion sheath or cover can be disposed over the catheter 310 that can force or otherwise cause the catheter 310 to assume a linear or substantially linear shape for insertion. A guide wire, stylet, or insertion aid (e.g., an outer insertion sheath) can also be configured to force the preformed catheter 310 into a non-linear shape (e.g., a hooked or arcuate shape) that can be advantageous for introduction into a body cavity. Following removal of the guide wire, stylet, or other insertion aid (e.g., after insertion into the body of a patient) the preformed catheter 310 can resiliently assume a third state as the catheter 310 (or the material of the catheter 310) at least partially recovers (or tries to recover) to its predetermined shape (or the configuration of the first state) as it transitions from a non-relaxed state (e.g., an insertion state) to a relaxed state (e.g., an inserted state). As can be appreciated, the third state may be slightly (or substantially) different than the predetermined shape of the first state, at least in part due to the constraints of the patient's 10 anatomy within which the catheter is disposed. The catheter 310 may also not perfectly recover to the configuration of the first state. In some embodiments, the configuration of the catheter 310 in the third state (e.g., a deployed state) can be described as being in an intermediate configuration that is between the first state (e.g., a state prior to deployment) and the second state (e.g., a deployment state).

In further embodiments, the preformed catheter 310 is capable of being straightened or substantially straightened as it is inserted into the body of a patient without an insertion aid. After insertion into the body of a patient, the preformed catheter 310 can resiliently assume (or at least partially assume) its predetermined shape as it transitions from a non-relaxed state (insertion state) to a relaxed state (inserted state).

Use of a preformed catheter can be advantageous in many ways. In certain embodiments, for example, the preformed catheter 310 can be configured to fill or extend through various regions within the body cavity. Further, the preformed shape can be configured such that the distal openings 324 are disposed in various regions of the body cavity of the patient. Having distal openings 324 disposed in different regions is advantageous in many ways. For example, as can be appreciated, one or more gases in the body cavity (e.g., stomach) of the patient can move into an upper region of the stomach, while the lower region can be filled with liquid or solid substances (e.g., food). Further, as the patient is moved (e.g., from an upright position to a horizontal or laying down position) the location of the one or more gases can also change. Having distal openings 324 disposed in multiple locations can help proper venting or aspiration, as one or more distal openings 324 can be kept out of the liquid region and in contact with a gas filled region, regardless of the orientation or position of the patient. In certain embodiments, one or more openings (e.g., a first distal opening) are also disposed in a different orientation or direction than one or more other distal openings (e.g., a second distal opening).

As previously indicated, in certain embodiments the preformed catheter assumes a helical, a spiral, or a coil-like shape in its relaxed state. In such embodiments, the distal openings 324 can be disposed in one or more of the upper region, lower region, left region, and right region of the body cavity (e.g., stomach) of the patient, allowing gases to be withdrawn from any one of such regions. In some embodiments, one or more dimensions of the preformed geometry exceeds the dimensions of the body cavity, causing the preformed catheter 310 to position or otherwise dispose itself in the outer (or peripheral) regions of the body cavity due to being constrained by the cavity walls.

In other embodiments, the one or more distal openings can be disposed in one or more regions of the body cavity (e.g., stomach), such as the upper region, lower region, left region, and right region, without the use of a preformed catheter. For example, in some embodiments the one or more distal openings are disposed on the catheter such that at least one opening is disposed in an upper region of the body cavity (e.g., stomach) following insertion in a patient. In further embodiments, the one or more distal openings can be disposed along a length of the catheter (e.g., along the intermediate section of the catheter) such that one or more distal openings are disposed in at least two regions of the body cavity (e.g., stomach). For instance, the one or more distal openings can be disposed along a length of the catheter such that at least one opening is disposed in a lower or intermediate region of the body cavity (e.g., stomach) and at least one opening is disposed in an upper region of the body cavity (e.g., stomach). In still further embodiments, bending and/or folding of the catheter following insertion into the body cavity can also cause the one or more distal openings to be disposed in one or more regions of (or throughout) the body cavity.

FIG. 7 depicts a preformed catheter 410 portion of a catheter assembly 400 in accordance with an embodiment of the present disclosure. As shown in FIG. 7, the catheter assembly 400 can comprise a preformed catheter 410 having openings 424 disposed in a variety of locations. In the illustrated embodiment, the preformed catheter 410 also assumes an undefined three-dimensional shape. Any variety of non-linear shapes (e.g., non-linear three-dimensional shapes) is contemplated.

FIG. 8 is a perspective view of a multi-lumen catheter assembly 500, according to another embodiment of the present disclosure. As shown in FIG. 8, the catheter assembly 500 can be disposed such that the distal end 512 of the catheter 510 is disposed in a bowel 14 or intestine of the patient 10. In such embodiments, the delivery of food can be to a bowel 14 or intestine region. Further, in certain of such embodiments, one or more distal openings 524 can be disposed in the stomach 12, such that venting and/or aspiration can simultaneously occur from within the stomach 12 region. One or more distal openings 524 can also be disposed in the bowel 14 region, if desired.

Figure 9:
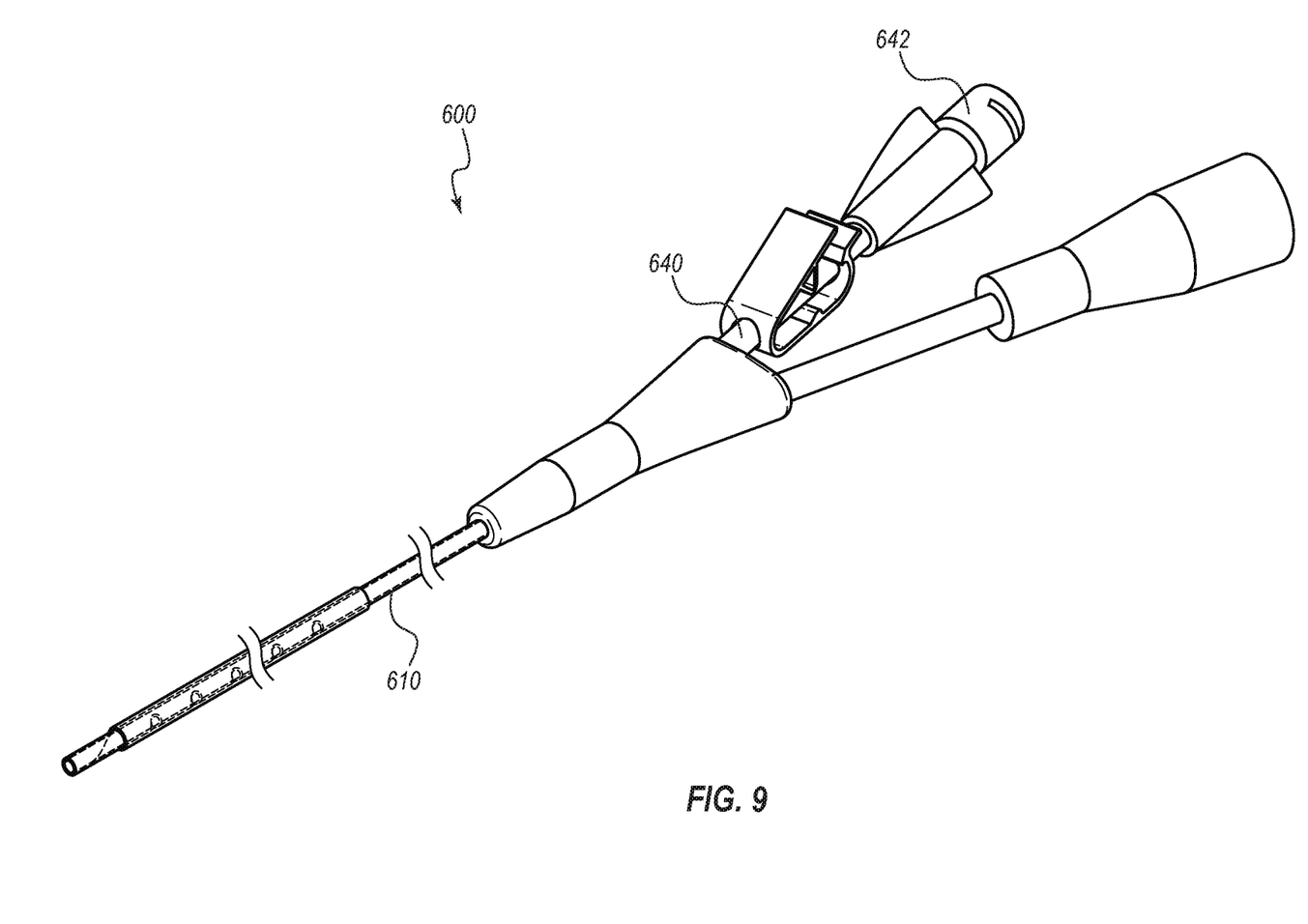
FIG. 9 is a perspective view of a multi-lumen catheter assembly, according to another embodiment of the present disclosure.

FIG. 9 is a perspective view of a multi-lumen catheter assembly 600, according to yet another embodiment of the present disclosure. As shown in FIG. 9, in some embodiments an enteral connector 642 is used. Other types of connectors that satisfy standards and/or international standards (e.g., ISO 80369-3) for feeding tubes and catheters can also be used. For example, various connectors (e.g., enteral connectors 642) that have selective compatibility can be used to reduce and/or minimize the risk of misconnections to the feeding lumen. With continued reference to FIG. 9, in some embodiments an enteral connector 624 can be coupled to a first extension leg 640. The enteral connector 642 can also be configured to couple to a feed system, and can be associated with the delivery of food through the multi-lumen catheter 610.

Figure 10:
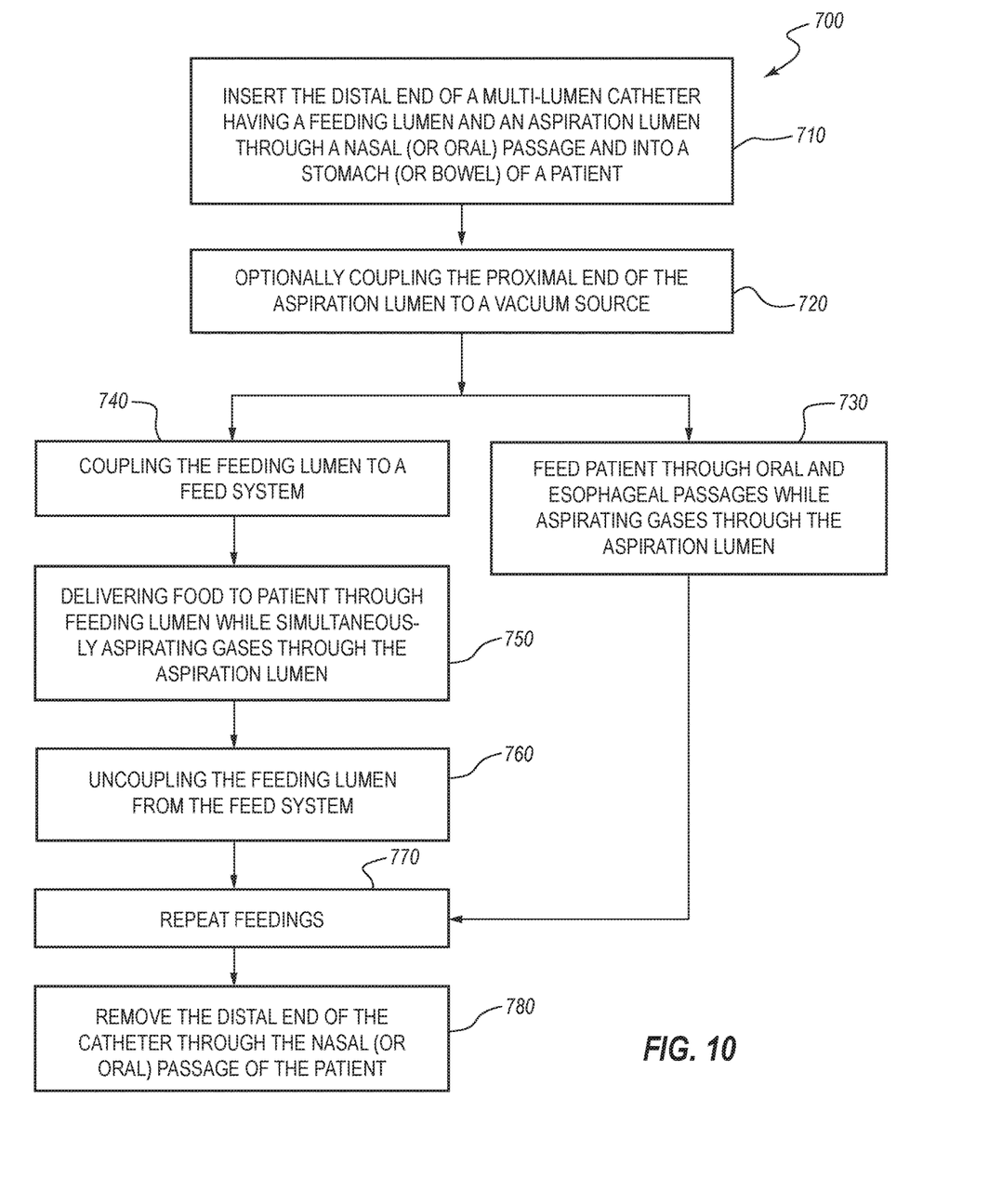
FIG. 10 is a flowchart of a method of using a multi-lumen catheter assembly, according to another embodiment of the present disclosure.

Methods of using the catheter assemblies are also disclosed herein. In particular, it is contemplated that any of the components, principles, and/or embodiments discussed above may be utilized in either a catheter assembly or a method of using the same. An illustrative method of using a catheter assembly, according to one embodiment of the present disclosure is depicted in FIG. 10. As shown in FIG. 10, in some embodiments the method 700 comprises a step 710 of inserting the distal end of a multi-lumen catheter having a feeding lumen and an aspiration lumen through a nasal (or oral) passage and into a stomach (or bowel) of a patient. The method 700 can further including a step 720 of coupling or otherwise connecting the proximal end of the aspiration lumen to a vacuum source, wherein the vacuum source is configured to reduce pressure in at least a portion of the aspiration lumen, causing one or more gases to be drawn from the patient into the aspiration lumen. In other embodiments, the proximal end of the aspiration lumen is left open to vent.

In one embodiment, the method 700 can comprise a step 740 of coupling or otherwise connecting the feeding lumen to a feed system, and a step 750 of delivering food from the feed system through the feeding lumen and into the patient while simultaneously venting or aspirating gases from the patient through the aspiration lumen. In certain embodiments, the method further comprises a step 760 of uncoupling the feeding lumen from the feed system. As can be appreciated, the aspiration lumen can be left venting or aspirating after the feed system has been uncoupled. The method can further comprise a step 770 of repeating the feeding steps 740, 750, and 760.

In particular embodiments, the method can comprise an alternate feeding step in place of, or in addition to, feeding steps 740, 750, and 760. For example, the method can comprise a step 730 of feeding the patient through oral and esophageal passages while venting or aspirating gases through the aspiration lumen. As desired, the method can also comprise a step 780 of removing the distal end of the catheter through the nasal (or oral) passage of the patient. Other method steps can also be employed.

Without limitation, it will be appreciated that the embodiments and disclosure herein can be applied to various types and/or sizes of multi-lumen catheters. For example, in some embodiments, the multi-lumen catheters have an outside diameter that is 10 french, 8 french, or 6 french or less. Other sizes of catheters can also be used.

Additionally, it will be appreciated that various materials can be used in forming the catheter assemblies. For example, in certain embodiments, the various components of the catheter assemblies, such as the catheter, the junction hub, the extension legs, and/or the connectors, can be made of one or more polymeric materials. Different polymeric materials can also be used for different components depending on, for example, the desired stiffness or flexibility of a given component. The various components can also be made in various ways, including but not limited to extrusion techniques, injection molding techniques, and other techniques known in the art.

Moreover, references to approximations are made throughout this specification, such as by use of the terms "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially linear" is recited with respect to a feature, it is understood that in further embodiments, the feature can have a precisely linear configuration.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. The scope of the invention is therefore defined by the following claims and their equivalents.

What is claimed is:

1. A catheter assembly, comprising:
   a multi-lumen gastrointestinal catheter, comprising:
      a feeding lumen;
      a first proximal opening that is in fluid communication with the feeding lumen, wherein the first proximal opening extends through a first connector;
      a first distal opening that is in fluid communication with the feeding lumen, wherein the first distal opening is configured to allow passage of liquid food out of the feeding lumen;
      an aspirating lumen;
      a second proximal opening that is in fluid communication with the aspirating lumen, wherein the second proximal opening extends through a second connector, the second connector being a different type of connector than the first connector; and
      a second distal opening that is in fluid communication with the aspirating lumen, wherein the second distal opening is configured to allow passage of one or more gases into the aspirating lumen;
   a membrane filter that is permeable to the one or more gases and impermeable to liquids and solids, wherein the membrane filter is positioned to restrict the passage of liquids and solids through the second distal opening and into the aspirating lumen;
   wherein the catheter assembly is configured to be coupled to a vacuum source, wherein the vacuum source is configured to reduce pressure in at least a portion of the aspirating lumen, wherein the catheter assembly is configured such that the membrane filter does not prohibit flow of the one or more gases through the aspirating lumen when the portion of the aspirating lumen is under reduced pressure, and
   wherein the catheter is configured to allow passage of food out of the feeding lumen and allow passage of one or more gases into the aspirating lumen simultaneously within a stomach of a patient.

2. The catheter assembly of claim 1, further comprising a venting lumen, wherein the venting lumen is in fluid communication with ambient conditions outside of the patient.

3. The catheter assembly of claim 1, further comprising a food source coupled to the first connector.

4. The catheter assembly of claim 1, wherein the vacuum source is configured to reduce pressure in at least the portion of the aspirating lumen intermittently.

5. The catheter assembly of claim 1, wherein the catheter is a preformed catheter that assumes a non-linear three-dimensional configuration when the catheter is in a relaxed state.

6. A catheter assembly, comprising:
   a multi-lumen gastrointestinal catheter, comprising:
      a feeding lumen coupled to a feed system;
      a first distal opening that is in fluid communication with the feeding lumen, wherein the first distal opening is configured to allow passage of food out of the feeding lumen;
      a venting or aspirating lumen;
      a second distal opening that is in fluid communication with the venting or aspirating lumen, wherein the second distal opening is configured to allow passage of one or more gases into the venting or aspirating lumen;
      a third distal opening, wherein the third distal opening extends through a side wall of the catheter and is in fluid communication with the venting or aspirating lumen; and
   a membrane filter that is permeable to one or more gases and impermeable to liquids and solids, wherein the membrane filter is positioned to restrict the passage of liquids and solids through at least one of the second or third distal openings and into the venting or aspirating lumen;
   wherein the catheter is configured to allow passage of food out of the feeding lumen and allow passage of one or more gases into the venting or aspirating lumen simultaneously within a stomach of a patient.

7. The catheter assembly of claim 6, further comprising a second venting or aspirating lumen, wherein the second venting or aspirating lumen is in fluid communication with ambient conditions outside of the patient.

8. The catheter assembly of claim 6, wherein the membrane filter is positioned to restrict the passage of liquids and solids through the second and third distal openings and into the venting or aspirating lumen.

9. The catheter assembly of claim 6, wherein the third distal opening is oriented in a different direction than the second distal opening.

10. The catheter assembly of claim 6, wherein the membrane filter comprises a polymeric material.

11. The catheter assembly of claim 6, wherein the membrane filter comprises a pore size of less than about 100 microns.

12. The catheter assembly of claim 6, wherein the membrane filter is coupled to the catheter using at least one of an adhesive, a heat seal, or a mechanical coupling member.

13. The catheter assembly of claim 6, wherein the catheter assembly is further coupled to a vacuum source, and wherein the vacuum source is configured to reduce pressure in at least a portion of the venting or aspirating lumen.

14. The catheter assembly of claim 13, wherein the feed system is configured to deliver food into the feeding lumen and the vacuum source is configured to reduce pressure in at least a portion of the venting or aspirating lumen simultaneously.

15. A method of using the catheter assembly of claim 1, comprising:
- inserting a distal end of the multi-lumen gastrointestinal catheter through a nasal or oral passage and into a stomach or bowel of a patient;
- coupling a feed system to the multi-lumen catheter such that the feed system is in fluid communication with the feeding lumen;
- delivering food from the feed system through the feeding lumen and into the patient; and
- venting or aspirating one or more gases from the patient through the aspirating lumen, wherein delivering food and venting or aspirating one or more gases occurs simultaneously.

16. The method of claim 15, further comprising:
- coupling a vacuum source to the multi-lumen gastrointestinal catheter such that the vacuum source is in fluid communication with the aspirating lumen, wherein the vacuum source is configured to reduce pressure in at least a portion of the aspirating lumen to cause the one or more gases to be drawn from the patient into the aspirating lumen.

17. The method of claim 16, wherein the vacuum source is configured to apply an intermittent vacuum to the aspirating lumen.

* * * * *